(12) United States Patent  
Miyoshi et al.

(10) Patent No.: US 8,462,352 B2  
(45) Date of Patent: Jun. 11, 2013

(54) SURFACE INSPECTION TOOL AND SURFACE INSPECTION METHOD

(75) Inventors: Yuji Miyoshi, Hitachinaka (JP); Tomohiro Funakoshi, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/450,226

(22) Filed: Apr. 18, 2012

(65) Prior Publication Data

US 2012/0262723 A1    Oct. 18, 2012

Related U.S. Application Data

(63) Continuation of application No. 12/979,885, filed on Dec. 28, 2010, now Pat. No. 8,189,205, which is a continuation of application No. 12/353,515, filed on Jan. 14, 2009, now Pat. No. 7,884,948.

(30) Foreign Application Priority Data

Jan. 17, 2008 (JP) ................................. 2008-008204

(51) Int. Cl.  
  *G01B 11/30* (2006.01)
(52) U.S. Cl.  
  CPC ..................................... *G01B 11/30* (2013.01)  
  USPC ....................................................... 356/600
(58) Field of Classification Search  
  CPC ...................................................... G01B 11/30  
  USPC ................................... 356/237.1–237.5, 600  
  See application file for complete search history.

(56) References Cited

U.S. PATENT DOCUMENTS

| 4,526,468 | A | 7/1985 | Steigmeier et al. |
| 6,826,735 | B2 | 11/2004 | Ono et al. |
| 7,295,300 | B1 * | 11/2007 | Bechtler et al. ............ 356/237.2 |
| 7,332,359 | B2 | 2/2008 | Hamamatsu et al. |
| 7,369,703 | B2 * | 5/2008 | Yamaguchi et al. .......... 382/199 |

(Continued)

FOREIGN PATENT DOCUMENTS

| JP | 07-019844 | 1/1995 |
| JP | 2002-340537 | 11/2002 |

(Continued)

OTHER PUBLICATIONS

Entire Prosecution of U.S. Appl. No. 12/353,515 to Miyoshi, et al., filed Jan. 14, 2009, entitled "Surface Inspetion Tool and Surface Inspection Method."

(Continued)

*Primary Examiner* — Michael P Stafira  
(74) *Attorney, Agent, or Firm* — McDermott Will & Emery LLP (57) ABSTRACT

A surface inspection tool 110 measures scattering light intensity of scattering light generated by irradiated irradiation light in association with a measurement coordinate on a wafer 200 with patterns and inspects the surface roughness of the wafer 200. The surface inspection tool includes a controller 250 which extracts measurement coordinate of the measured scattering light intensity that is equal to or more than a lower limit threshold L, sets an inspection range 406 of the surface roughness inspection in a partial layout 405a of a part of the whole layout 401 of the pattern corresponding to the periphery of the extracted measurement coordinate, and obtains the surface roughness in the inspection range 406.

8 Claims, 9 Drawing Sheets

U.S. PATENT DOCUMENTS

| | | |
|---|---|---|
| 7,499,583 B2 | 3/2009 | Alumot et al. |
| 7,884,948 B2 | 2/2011 | Miyoshi et al. |
| 2004/0263834 A1 | 12/2004 | Alumot et al. |
| 2005/0185172 A1 | 8/2005 | Ishimaru et al. |
| 2007/0071308 A1 | 3/2007 | Nakatani |
| 2008/0013076 A1* | 1/2008 | Matsui ............................ 356/73 |
| 2008/0013083 A1* | 1/2008 | Kirk et al. ................... 356/237.5 |
| 2008/0068593 A1* | 3/2008 | Nakano et al. ................... 356/73 |
| 2008/0304055 A1* | 12/2008 | Oshima et al. ............. 356/237.5 |
| 2009/0103078 A1 | 4/2009 | Ishimaru et al. |

FOREIGN PATENT DOCUMENTS

| | | |
|---|---|---|
| JP | 2003-35680 | 2/2003 |
| JP | 2006-064496 | 3/2006 |
| JP | 2007-88617 | 4/2007 |

OTHER PUBLICATIONS

Entire Prosecution of U.S. Appl. No. 12/979,885 to Miyoshi, et al., filed Dec. 28, 2010, entitled "Surface Inspection Tool and Surface Inspection Method."

* cited by examiner

404
Memory pattern

FIG. 5C

405
Logic pattern

| Sequential serial number 901 | Inspection tool image 902 | | | Review image 903 | | CAD data 904 | Scattering light intensity 905 | | |
| --- | --- | --- | --- | --- | --- | --- | --- | --- | --- |
| | t1 | t2 | t3 | First | Second | | t1 | t2 | t3 |
| n1 | ~ | ~ | ~ | ~ | | ~ | 32 | 31 | 28 |
| n2 | ~ | ~ | ~ | | | | | 26 | |
| n3 | ~ | ~ | ~ | | | | 30 | | 31 |
| n4 | ⊥ | ⊥ | ⊥ | ⊥ | ~ | ⊥ 801 | 30 | 35 | 40 |
| n5 | | | | ~ | ~ | ~ | 24 | | |
| n6 | | | | | | | 20 | | 22 |
| n7 | | | ~ | | | | | 37 | |
| n8 | ~ | ~ | ~ | | | | | | 30 |
| n9 | | | | | ~ | | 28 | | |

906

Inspection conditions
☐ Condition t1
☐ Condition t2
☑ Condition t3
910

Inspection execution 913

911

SURFACE INSPECTION TOOL AND SURFACE INSPECTION METHOD

This application is a Continuation of U.S. application Ser. No. 12/979,885, filed on Dec. 28, 2010, now U.S. Pat. No. 8,189,205, which is a Continuation of U.S. application Ser. No. 12/353,515, filed on Jan. 14, 2009, now U.S. Pat. No. 7,884,948, claiming priority of Japanese Patent Application No. 2008-008204, filed on Jan. 17, 2008, the entire contents of each of which are hereby incorporated reference.

BACKGROUND OF THE INVENTION

1. Field of the Invention

The present invention relates to a surface inspection tool and a surface inspection method, both of which are used for inspection of a wafer with patterns.

2. Description of the Related Art

In recent years, design rule shrinkage in leading edge semiconductor devices (apparatuses) has been pursued to the maximum, and not only the design rule shrinkage of pattern line widths but also thin film realization of produced films has been performed. In the case of a gate oxide film, a thin film having a film thickness of 1 to 2 nm is used and the film thickness comes close to the magnitude of irregularities (surface roughness) of a film surface. Therefore, the ratio of variation film thickness which locally varies depending on the surface roughness to the film thickness increases; and therefore, the surface roughness of the film surface which has not been brought problem in the conventional semiconductor devices is starting to have a large influence on the characteristics in the leading edge semiconductor devices.

Furthermore, configurations of wafer processing apparatuses used for manufacturing semiconductor devices have also been changed. For example, in a gate oxide film formation process, conventionally, there is a general mode in which several tens to about one hundred of wafers are processed in block by using a vertical type oxidation diffusion apparatus. However, nowadays, the use of an oxidation diffusion apparatus of sheet process suitable for large diameter realization of wafers has been rapidly spread; and consequently, variations in film thickness and surface roughness between the wafers due to the sheet process becomes one factor of degradation in yield of the semiconductor devices.

Therefore, in the production process of the leading edge semiconductor devices, it is necessary to set production conditions which does not easily cause variations in the film thickness and surface roughness of the produced films, and to strictly control the film thickness and surface roughness of the produced films manufactured under the production conditions.

As technology for measuring the surface roughness of the conventional wafer, there are proposed the following methods: (1) a method in which a wafer is cut or processed by focused ion beam (FIB) process and the cut surface is observed with an electron microscope; (2) a method in which surface roughness of a wafer is measured with an atomic force microscope (AFM); (3) a method in which laser light is made incident on a wafer surface and scattering light caused by the surface roughness from the wafer surface is received to measure the surface roughness of the wafer, as disclosed in Japanese Patent Application Laid open (JP-A) No. 2006-64496A1 and JP-A No. 2002-340537A1. Furthermore, in JP-A No. 7-19844A1, there is proposed a method in which an X-ray is used in place of laser light.

SUMMARY OF THE INVENTION

However, considering that surface roughness of a wafer with patterns at a process in mid-flow is measured, the prior arts have the following problems: the FIB process described in (1) is a destructive inspection, and therefore, a semiconductor device cannot be manufactured from the wafer having been used for the inspection; furthermore, in the AFM described in (2), a step due to a pattern is larger by a magnitude of several digits as compared with a step due to the surface roughness, and therefore, in the measurement of the surface roughness in a region having the step of the pattern, measurement accuracy of the surface roughness is degraded by measurement of the step of the pattern; and besides, in the method which receives the scattering light described in (3), scattering light caused by a step of a pattern becomes noise, and therefore, measurement accuracy of the surface roughness of the wafer is degraded.

However, in the wafer with patterns, it is not necessarily the case that the surface roughness of the wafer cannot be measured by the methods of (2) and (3); however, a flat inspection range having the area necessary for measurement is placed at some place in the wafer surrounded by the patterns, and the surface roughness in the flat inspection range is measured; and accordingly, net surface roughness having no effect of the pattern can be measured.

However, conventionally, the flat inspection range is searched by only visual search, and much time is required for this search. Furthermore, this search is manual search; and therefore, it is also not possible to automatically perform online measurement. From these points of view, in order to measure the surface roughness of the wafer with patterns with high accuracy and in a nondestructive manner, it is considered that it is necessary to establish means capable of searching the flat inspection range without depending on the visual search.

Consequently, an object of the present invention is to solve the problem and to provide a surface inspection tool and a surface inspection method, in which a flat inspection range capable of measuring surface roughness of a wafer with patterns with high accuracy and in a nondestructive manner can be searched without visual search.

According to the present invention which has solved the problem, in a surface inspection tool and a surface inspection method, which measure scattering light intensity of scattering light generated by irradiated irradiation light in association with a measurement coordinate on a wafer with patterns and inspect surface roughness of the wafer, a controller extracts the measurement coordinate of a location in which the measured scattering light intensity is equal to or more than a lower limit threshold, sets an inspection range of the surface roughness inspection in a partial layout of a part of the whole layout of the pattern corresponding to the periphery of the extracted measurement coordinate, and obtains the surface roughness in the inspection range.

According to the present invention, there can be provided a surface inspection tool and a surface inspection method, in which a flat inspection range capable of measuring surface roughness of a wafer with patterns with high accuracy and in a nondestructive manner can be searched without visual search.

DESCRIPTION OF REFERENCE NUMERALS

100 Measurement tool group of wafer surface roughness
101 Surface inspection system
110 Optical wafer surface inspection tool (surface inspection tool)
120 Data server
121 List display database
130 Design information database
140 Network
200 Wafer
210 Sample inspection table
211 Sample stage
212 Rotational shaft
213 Motor spindle
214 Linear motor
220 Illumination light source
221 Illumination light
230 Scattering light detector
231a to 231d Detector
232a to 232d Amplifier
233a to 233d A/D converter
240 Signal processing part
250 Tool controller
260 Stage controller
270 Information display unit
280 Input operation unit
290 Storage unit
295 Communication unit
301, 301a, and 301b Foreign particle
W301a and W301b Foreign particle signal (scattering light intensity)
302 Defect
W302 Defect signal (scattering light intensity)
310 and 311 Flat portion
W310 and W311 Flat portion signal (scattering light intensity)
320 Scattering light intensity distribution view
401 Chip to be inspected (whole layout)
402 and 402a Memory unit
403 and 403a Logic unit
404 Memory pattern
404a Partial layout
405 Logic pattern
405a Partial layout
406 Inspection range
501 Scattering light intensity of memory unit
502 Scattering light intensity of logic unit
503 Scattering light intensity of inspection range
504 Foreign particle signal
505 Defect signal
601 Scanned result display screen (GUI) for one chip
602 Contour chart display window
603 Display window of the whole layout of chip
604 Histogram display window
605 Enlarged display window of partial layout
606 SET button
607 Extraction button
608 Assist tool button
609 Contour chart
610 Histogram
611 Spectrum with low pattern density
612 Foreign particle or defect spectrum
613 and 614 Spectrum with high pattern density
701 Scattering light intensity focusing window
702L Lower limit threshold setting column
702H Upper limit threshold setting column
703 Registration button
704 Cancel button
801 Partial layout
900 Assist tool display screen (GUI)
901 Sequential serial number display column
902 Inspection tool image display column
903 Review image display column
904 Partial layout (CAD data) display column
905 Scattering light intensity display column
906 Object coordinate selection check column
910 Inspection condition selection check column
911 Scroll bar
913 Inspection execution button

DETAILED DESCRIPTION OF THE PREFERRED EMBODIMENTS

Next, an embodiment of the present invention will be described with appropriate reference to the drawings. In addition, the same reference numerals are given to common portions in the respective drawings and their detail description will not be repeated.

Figure 1:
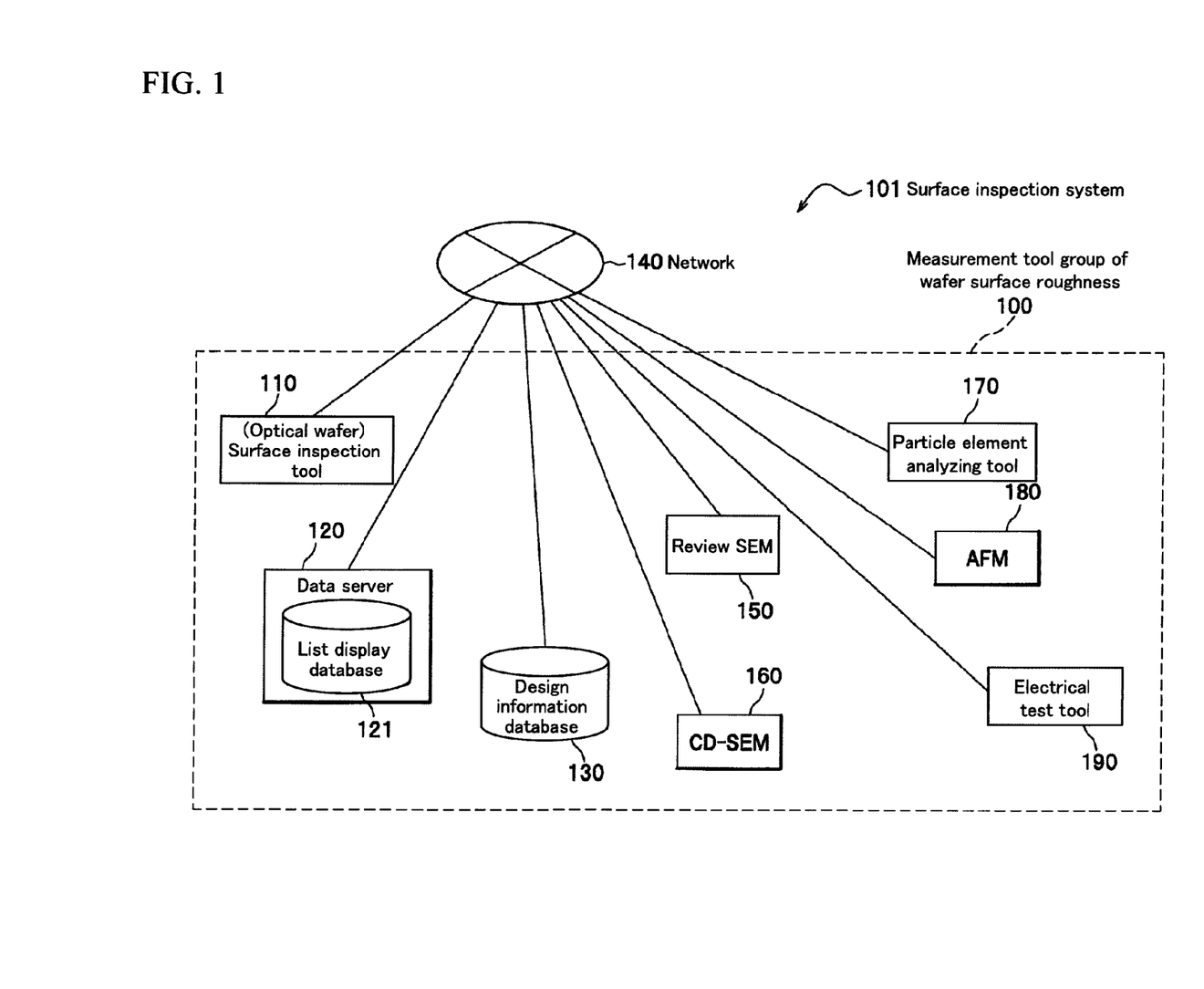
FIG. 1 is a configuration view of a surface inspection system which has a surface inspection tool according to an embodiment of the present invention.

FIG. 1 shows a configuration view of a surface inspection system 101. The surface inspection system 101 includes a measurement tool group of wafer surface roughness 100 composed of an optical wafer surface inspection tool 110, a data server 120, a design information database 130, a review scanning electron microscope (SEM) 150, a critical dimension-SEM (CD-SEM) 160, a particle element analyzing tool 170, an AFM 180, an electrical test tool 190, and the like; and the respective devices are connected via a network 140 each other.

The optical wafer surface inspection tool 110 has means which irradiates a wafer surface with light impinging on the wafer to be scattered and obtains both the intensity of scattering light (scattering light intensity) and a location (measurement coordinate) where the irradiation and the scattering are performed. In addition, in the embodiment, there will be described a case where the surface inspection tool of the present invention is mainly used in the optical wafer surface inspection tool 110. Conventionally, it is not possible to measure surface roughness of a wafer with patterns because scattering light due to a concave and convex portion (step) of the pattern becomes noise; however, in the optical wafer surface inspection tool 110, a flat inspection range capable of measuring wafer surface roughness on the wafer with patterns is pre-scanned, and a candidate for the flat inspection range are displayed on the basis of its scattering light intensity distribution while being superimposed on the whole layout of a semiconductor device; and accordingly, a user can promptly and surely designate the inspection range from the candidates. Then, in the optical wafer surface inspection tool 110, the surface roughness of the wafer with patterns can be automatically measured by using the inspection range. In the case of the flat inspection range, scattering light due to the pattern step is not generated; and therefore, the surface roughness of the wafer can be measured with high accuracy. Furthermore, the user does not need to search the whole range of the semiconductor device, but may search the candidates for the inspection range; and therefore, the flat inspection range can be promptly searched.

The data server 120 is a computer which can store data such as measurement data obtained from the optical wafer surface inspection tool 110; measurement data of the review SEM 150, the CD-SEM 160, and the AFM 180; test data of the electrical test tool 190; and analysis data of the particle element analyzing tool 170, in association with an identifier of the wafer. Furthermore, the data server 120 stores an identifier of the semiconductor device manufactured on the wafer in association with the identifier of the wafer. The data server 120 has a list display database 121, and the list display database 121 saves a list display being made on the basis of the measurement data saved in the data server 120. Then, an identifier of a wafer to be inspected is obtained, and the identifier of the semiconductor device manufactured on the wafer to be inspected can be read out on the basis of the identifier of the wafer to be inspected. In addition, the detail of the list display will be described later.

The design information database 130 is a database which saves design (CAD) data of the wafer; and, for example, design information data such as layout data (floor plan data) of a functional block such as a memory unit and a logic unit which constitute the semiconductor device (chip); mask data for fanning layers such as an active layer and a wiring layer of the semiconductor device, which is made as a result of layout based on the layout data; configuration data of the pattern which the functional block has, that is, the semiconductor device has; arrangement data of the semiconductor devices on the wafer; positional data in a scribe region; and positional data of a TEG, are stored and saved in association with the identifier of the semiconductor device. Then, the whole layout (layout data) of the semiconductor device manufactured on the wafer to be inspected can be read out on the basis of the identifier of the semiconductor device manufactured on the wafer to be inspected. Furthermore, the configuration data of the pattern of the semiconductor device on the periphery of the measurement coordinate can be read out on the basis of the measurement coordinate.

The review SEM 150 is a tool which makes an observation and a classification of a foreign particle or a defect on the wafer by using a scanning electron microscope. First, the optical wafer surface inspection tool 110 measures the presence or absence of the foreign particle or the defect and the measurement coordinate in which the foreign particle or the defect is observed. Then, the review SEM 150 observes the foreign particle or the defect and classifies them to identify occurrence reasons of the foreign particle or the defect on the basis of information of the measurement coordinate and the like.

The CD-SEM 160 obtains the identifier of the wafer to be inspected; reads out an identifier of the semiconductor device manufactured on the wafer on the basis of the identifier of the wafer to be inspected and, further, a measurement recipe which is for measuring the semiconductor device; and performs automatic measurement of line widths and spaces of patterns of the semiconductor device on the basis of the measurement recipe.

The particle element analyzing tool 170 is one which analyzes a foreign particle element and an energy dispersive X-ray spectrometer (EDX), for example. The foreign particle can be easily found on the basis of the information such as the measurement coordinate of the foreign particle observed by the optical wafer surface inspection tool 110; and therefore, the particle element analyzing tool 170 can promptly analyze the foreign particle element.

The AFM 180 is a tool which observes a surface state of the wafer (surface roughness) in non-contact and nondestructive manners by measuring atomic forces which the tip of a probe receives from the wafer surface. In addition, in the embodiment, there will be described a case where the surface inspection tool of the present invention is mainly used in the optical wafer surface inspection tool 110; however, the present invention is not limited to this, and the surface inspection tool of the present invention can be also used in the AFM 180. According to this, the flat inspection range can be found by searching; and therefore, the probe does not go over the step due to patterns, measurement accuracy of the measurement of the surface roughness can be increased. As described above, the surface inspection tool of the present invention can be used in various kinds of surface inspection tools which measure the surface roughness. It is considered that the optical wafer surface inspection tool 110 and the AFM 180 include the surface inspection tool of the present invention; however, the present invention is not limited to this, and the surface inspection tool of the present invention may be provided on the outside of the optical wafer surface inspection tool 110 or the AFM 180. However, a mechanical configuration of the surface inspection tool of the present invention is already provided in the optical wafer surface inspection tool 110; and therefore, the simplest and most secure implementation method is to implement the surface inspection tool of the present invention, for the optical wafer surface inspection tool 110.

The electrical test tool 190 is a tool which obtains an identifier of a wafer to be inspected; reads out the identifier of the semiconductor device manufactured on the wafer on the basis of the identifier of the wafer to be inspected and, further, reads out a test recipe which is for testing the semiconductor device; applies a signal waveform to the semiconductor device (chip) on the wafer on the basis of the test recipe; and compares an output waveform outputted from the chip at that time to a normal waveform preliminarily stored in the data server 120 or the electrical test tool 190.

The network 140 is a communication network by Ethernet (trademark), for example.

Next, the operation of the surface inspection system 101 will be described.

The optical wafer surface inspection tool 110 executes a surface inspection method of the present invention (to be described later) and measures surface roughness of a wafer; obtains arithmetic mean deviation of the profile Ra, root mean square roughness Rms, and the like which represent the surface roughness; and stores in the data server 120. The optical wafer surface inspection tool 110 can measure not only the surface roughness but also detect a foreign particle or a defect. In order to further investigate the foreign particle detected by the optical wafer surface inspection tool 110, a wafer to be inspected is moved to the review SEM 150 or the CD-SEM 160. This delivery may be manually or mechanically performed.

After the wafer to be inspected is moved to the review SEM 150 or the CD-SEM 160, an access is made from the review SEM 150 or the CD-SEM 160 to the data server 120, and an inspected result of the optical wafer surface inspection tool 110 is received from the data server 120 via the network 140. Then, review or length measurement is started by using the inspected result. At the time of performing the review or the length measurement, it is possible that an access is made to the design information database 130; search of a measurement coordinate, matching of positional information, and the like are performed from design information; the measurement coordinate is found out correctly and fast; and that the review or the length measurement is efficiently performed. At this time, information added by the optical wafer surface inspection tool 110 is used and a foreign particle against which a countermeasure is needed is preferentially reviewed; and accordingly, it becomes possible to promptly analyze the foreign particle which causes a fault. Furthermore, similarly, also in the particle element analyzing tool 170, the foreign particle can be easily searched and analyzed on the basis of the inspected result of the optical wafer surface inspection tool 110; and therefore, the analysis of the fault cause can be promptly advanced.

These review data and analysis result are saved in the data server 120 and are confronted with a test result in the electrical test tool 190; and accordingly, it is possible to confirm whether or not it finally becomes a fault. In the case where it does not finally become a fault, data for changing the standard for selecting the foreign particle against which the countermeasure is needed is transmitted to the optical wafer surface inspection tool 110 from the data server 120, and the standard of the optical wafer surface inspection tool 110 for determination whether a countermeasure is required or not is changed; and accordingly, it becomes possible to select the foreign particle against which the countermeasure is needed with high accuracy, and it becomes possible to promptly take the countermeasures against the fault during manufacturing of the semiconductor device.

In addition, the description is made by use of an example in which data such as the inspected result is sent and received via the network 140; however, it does not necessarily send and receive via the network 140, for example, it may be performed by data passing through a removable storage medium or a printed out paper copy.

Figure 2:
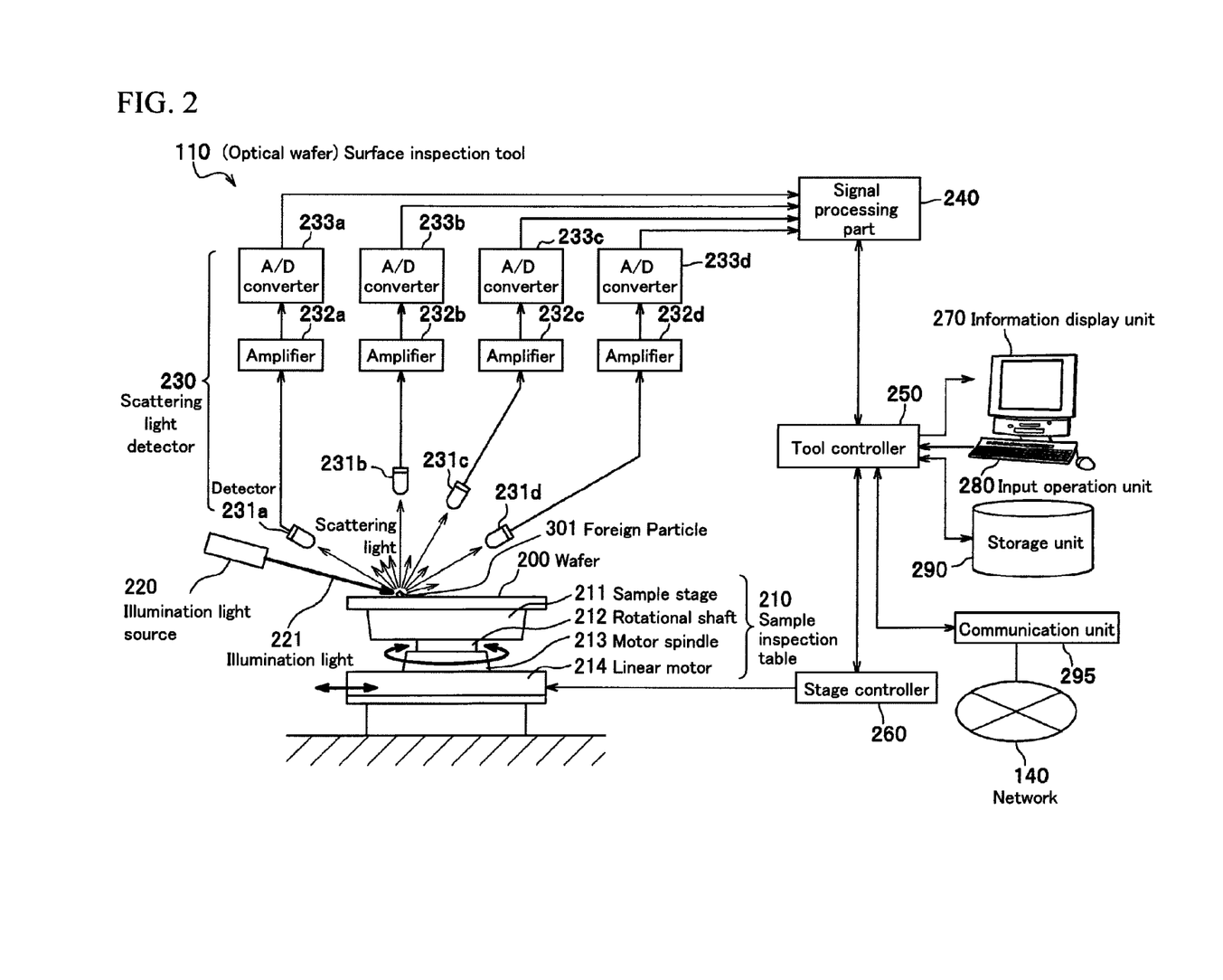
FIG. 2 is a configuration view of the surface inspection tool according to the embodiment of the present invention.

FIG. 2 shows a configuration view of the optical wafer surface inspection tool 110 (surface inspection tool of the present invention). The optical wafer surface inspection tool 110 comprises a sample inspection table 210, an illumination light source 220, a scattering light detector 230, signal processing part 240, a tool controller (corresponding to a controller stated in the appended claim 250, a stage controller 260, an information display unit 270, an input operation unit 280, a storage unit 290, and a communication unit 295.

The sample inspection table 210 includes a sample stage 211 on which a sample such as a wafer 200 is mounted, a motor spindle 213 which rotates the sample stage 211 around the center of a rotational shaft 212, and a linear motor 214 which moves the sample stage 211 in a radial direction.

In this case, the motor spindle 213 and the linear motor 214 are controlled by the stage controller 260 which receives a command signal from the tool controller 250.

The illumination light source 220 is placed so that irradiating light (illumination light 221) irradiates at a certain one point (spot) on the sample stage 211. Therefore, while the motor spindle 213 of the sample inspection table 210 rotates the rotational shaft 212 under the control of the stage controller 260, the linear motor 214 is moved in the radial direction; and accordingly, all measurement coordinates on the sample stage 211 can be served as a spot, and the illumination light 221 can be irradiated at the specific measurement coordinate of the wafer 200 on the sample stage 211.

Then, the specific measurement coordinate of the wafer 200 which is irradiated with the illumination light 221 can be converted into an XY coordinate by the stage controller 260 on the basis of a rotational angle of the motor spindle 213 and radial movement distance of the linear motor 214. Obtained XY coordinate data is saved in the storage unit 290 via the tool controller 250. In this case, in order to reduce a spot area as much as possible, high coherency light such as laser light is preferable for the illumination light 221.

The scattering light detector 230 has detectors 231a to 231d which detect scattering light. In FIG. 2, total four detectors of the detectors 231a and 231d disposed at a low angle position and the detectors 231b and 231c disposed at a high angle position are shown; however, there is no limitation in the number of the detectors 231a to 231d, there may be arranged two or more detectors so that the detectors 231a to 231d are different from each other in at least one of an azimuthal angle and an elevation angle of the direction from the spot to the detectors. The detectors 231a to 231d detect their respective scattering light generated at the spot on the surface of the wafer 200, which is irradiated with the illumination light (laser light) 221 from the illumination light source 220. A signal of a foreign particle or a defect (defect signal) and a surface roughness signal (haze signal) are included in detection signals outputted by the detectors 231a to 231d.

Furthermore, in the scattering light detector 230, the detectors 231a to 231d are connected to their respective amplifiers 232a to 232d, and in turn, connected to their respective A/D converters 233a to 233d. With this configuration, the detection signals of the detectors 231a to 231d are amplified by their respective amplifiers 232a to 232d, and are converted to digital signals in their respective A/D converters 233a to 233d.

The signal processing part 240 makes synthesized signals by combining the digitalized detection signals in accordance with calculation conditions (program) specified. Data of the synthesized signals combined by the signal processing part 240 and data of the digitalized detection signals which have been the basis for the synthesized signals are saved in the storage unit 290 via the tool controller 250. In addition, data of the synthesized signals includes scattering light intensity.

The tool controller 250 performs control of the whole optical wafer surface inspection tool 110, measures scattering light intensity of the scattering light resulted from the irradiated illumination light (irradiation light) 221 in association with a measurement coordinate on the wafer with patterns 200, and inspects surface roughness of the wafer 200. Furthermore, the tool controller 250 receives an operation signal from the input operation unit 280, performs processing corresponding to the operation signal by using the program stored in the storage unit 290, outputs the command signal on which the stage controller 260 performs control of the motor spindle 213 and the linear motor 214 which the sample inspection table 210 has, and changes calculation conditions which are for combining the digitalized detection signals by the signal processing part 240.

Furthermore, the tool controller 250 makes the storage unit 290 store the data of the synthesized signals combined by the signal processing part 240 and the data of the digitalized detection signals of the detectors 231a to 231d which are the basis for the synthesized signals; processes those data by using the processing program stored in the storage unit 290; and makes the information display unit 270 display them.

The input operation unit 280 is one by which a user inputs combination conditions of the detection signals by the signal processing part 240 and designates operations or the like of the respective devices, as described above.

The storage unit 290 stores the program and constant number necessary for various kinds of controls and calculation processes, measurement results (synthesized signals and detection signal), the combination conditions set by the input operation unit 280, and the like. The data of the synthesized signals and the data of the detection signals of the respective detectors 231a to 231d are stored together with the measurement coordinate of the scattering light on the wafer obtained from the stage controller 260.

The communication unit 295 is connected to the network 140, and the tool controller 250 performs sending and receiving of data with the data server 120 and the design information database 130 via the communication unit 295.

Next, a surface inspection method according to an embodiment of the present invention which is mainly performed by the tool controller 250 will be described.

Figure 3:
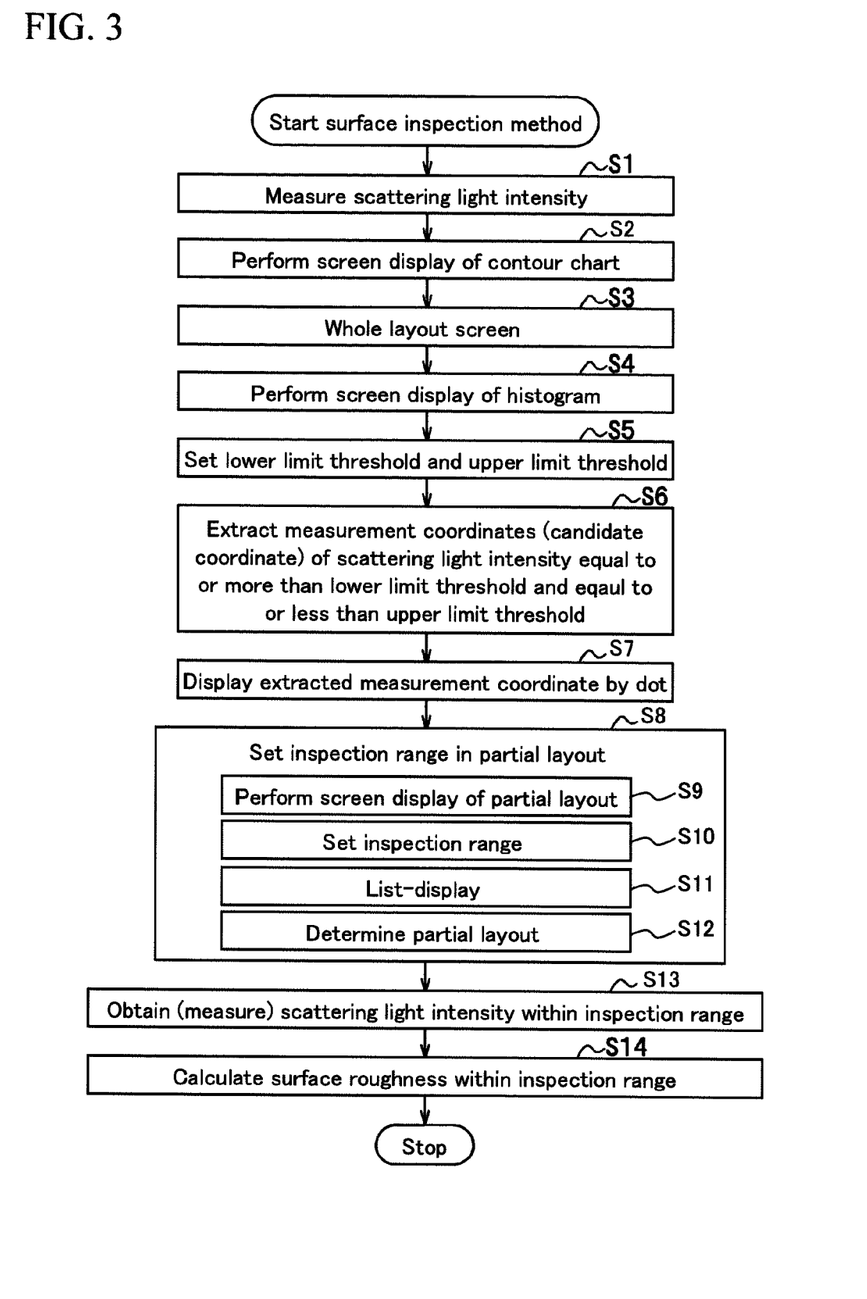
FIG. 3 is a flowchart of a surface inspection method according to an embodiment of the present invention.

FIG. 3 shows a flowchart of the surface inspection method according to the embodiment of the present invention.

First, at step S1, the tool controller 250 controls the whole optical wafer surface inspection tool 110, and measures scattering light intensity of scattering light resulted from the irradiated illumination light (irradiation light) 221 in association with a measurement coordinate on the wafer with patterns 200.

In this case, although it is in the middle of the description of the flowchart, the characteristics of the scattering light intensity will be described for ease of understanding the present invention.

Figures 4A, 4B:
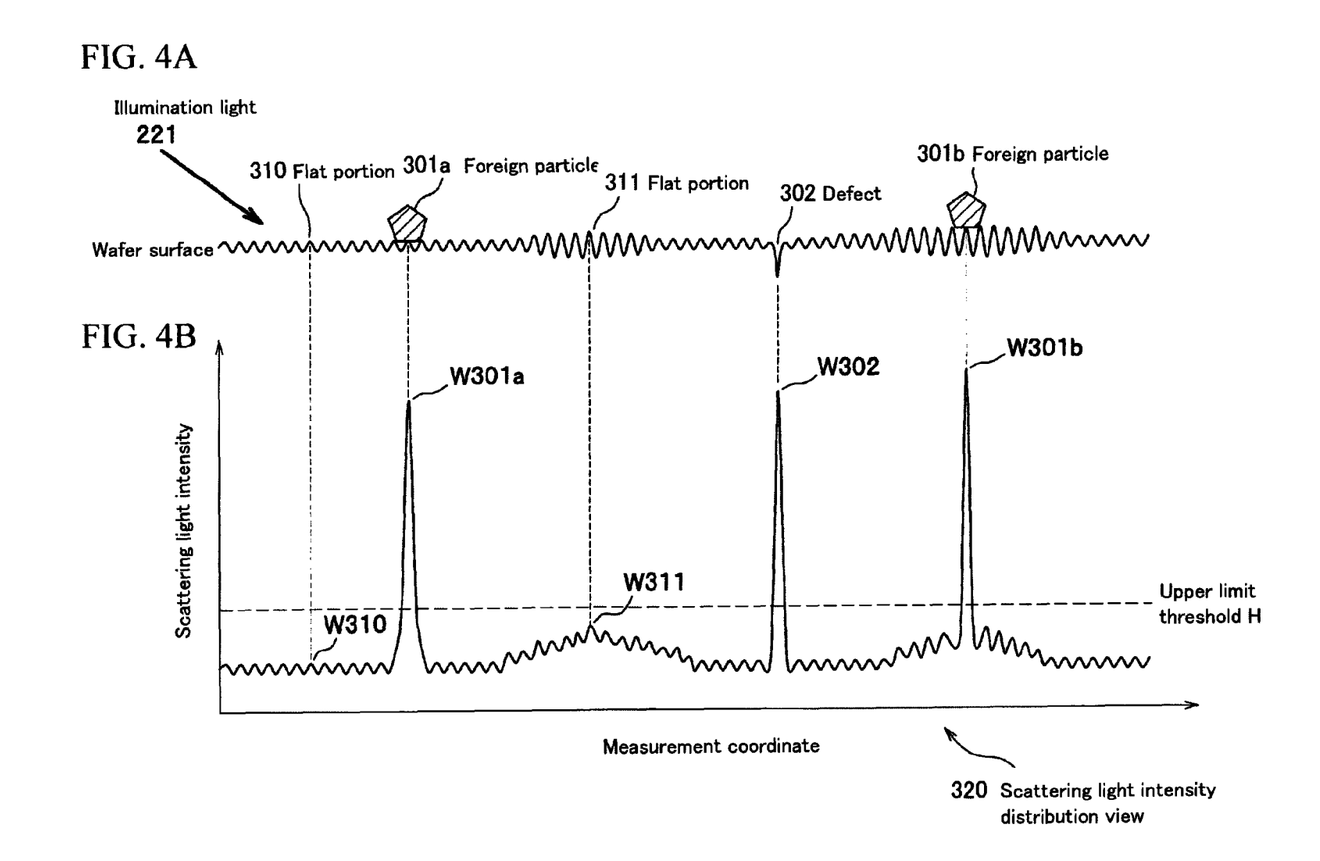
FIG. 4A is a schematic view of a region where there is no pattern on a wafer surface.
FIG. 4B is a scattering light intensity distribution view in measuring the region where there is no pattern on the wafer surface by using the surface inspection tool.

FIG. 4A shows a schematic view of a region where there is no pattern on the surface of the wafer 200. For example, foreign particles 301a and 301b are present and a defect 302 is generated on the surface of the wafer 200 that is an object to be measured. There exist irregularities corresponding to the surface roughness on flat portions 310 and 311 on the surface of the wafer 200. A step of the irregularities on the flat portion 310 is smaller than a step of the irregularities on the flat portion 311, and the surface roughness on the flat portion 310 becomes smaller.

FIG. 4B shows a scattering light intensity distribution view 320 in the case where the scattering light intensity is measured along the surface of the wafer 200 shown in FIG. 4A. Scattering light intensity W310 can be obtained from the scattering light generated at the flat portion 310 by irradiating the wafer 200 with the illumination light 221. Similarly, scattering light intensity W301a can be obtained from the foreign particle 301a; scattering light intensity W311 can be obtained from the flat portion 311; scattering light intensity W302 can be obtained from the defect 302; and scattering light intensity W301b can be obtained from the foreign particle 301b. Then, the scattering light intensity distribution view 320 can be made from the scattering light intensity for each of the measurement coordinates on the surface of the measured wafer 200.

In the scattering light intensity, foreign particle elements (W301a, W302, and W301b) are larger than surface roughness elements (W310 and W311); and therefore, the foreign particle elements (W301a, W302, and W301b) can be separated from the surface roughness elements (W310 and W311) by using an upper limit threshold H which can be designated by the input operation unit 280 shown in FIG. 2.

The scattering light intensity W310 of the surface roughness element (W310) is smaller than the scattering light intensity W311 of the surface roughness element (W311). For this reason, it shows that magnitude relation in the surface roughness is correlated to magnitude relation in the scattering light intensity. Then, the average of the scattering light intensity of all the surface roughness elements (W310 and W311) which are separated from the foreign particle element is taken; and accordingly, a Haze value of the average surface roughness on the surface of the wafer 200 that is the object to be measured can be obtained, and it becomes possible to compare the surface roughness among a plurality of the wafers 200.

The characteristics of the scattering light intensity of the region where there is no pattern on the semiconductor device (chip) has been described so far. Next, the characteristics of the scattering light intensity of a region where there is a pattern will be described.

Figure 5A:
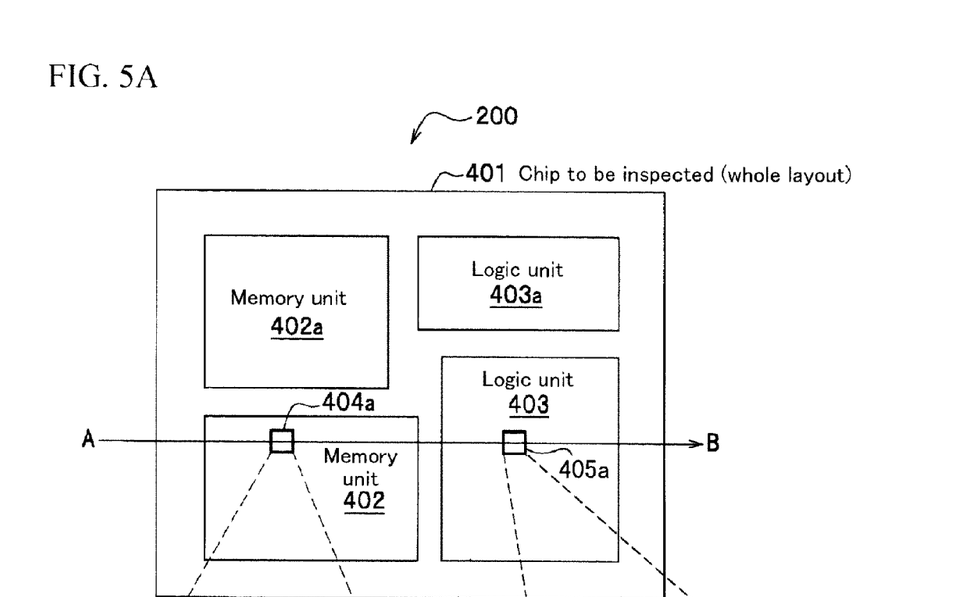
FIG. 5A is the whole layout showing a (layout) pattern of a chip to be inspected.
Figures 5B, 5C:
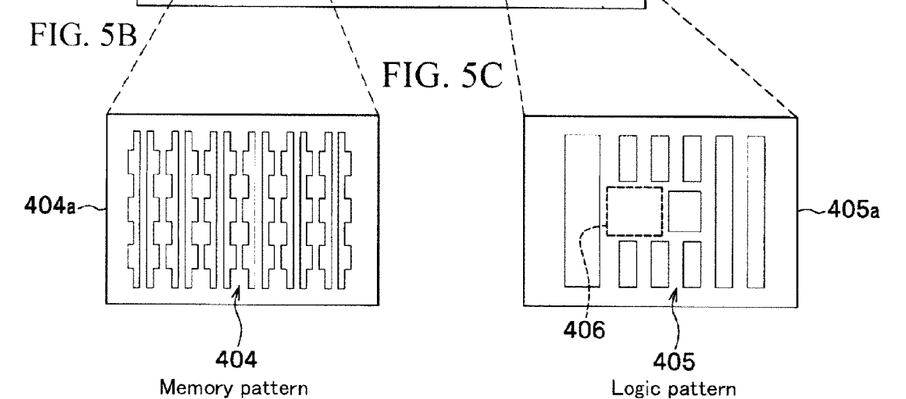
FIG. 5B is a partial layout showing a part of a memory unit.
FIG. 5C is a partial layout showing a part of a logic unit.

FIG. 5A shows one example of the whole layout of the (layout) pattern of a chip to be inspected of the semiconductor device. Generally, a chip to be inspected 401 is composed of a plurality of functional blocks such as memory units 402 and 402a and logic units 403 and 403a, and connection is made by wiring among the functional blocks. In many cases, as shown in a partial layout 404a in FIG. 5B, the partial layout 404a being a part of the memory unit 402 shown in FIG. 5A, a memory pattern 404 with a high repeatability is formed in the memory units 402 and 402a. The memory pattern 404 has a dense pattern configuration with a high occupation density of the pattern. On the other hand, as shown in a partial layout 405a in FIG. 5C, the partial layout 405a being a part of the logic unit 403 shown in FIG. 5A, a logic pattern 405 with low repeatability is formed in the logic units 403 and 403a. The logic pattern 405 has a sparse pattern configuration with a low occupation density of the pattern. Therefore, as shown in FIG. 5C, there are many cases where there exists a flat inspection range 406 capable of measuring surface roughness in the logic unit 403.

Measurement is performed by using the optical wafer surface inspection tool 110, and therefore, if a spot diameter of a laser beam that is the illumination light 221 is approximately 10 μm, a sufficient size capable of measuring the scattering light intensity distribution view 320, as the inspection region, is equal to or more than approximately 50 μm×50 μm.

Figure 6A:
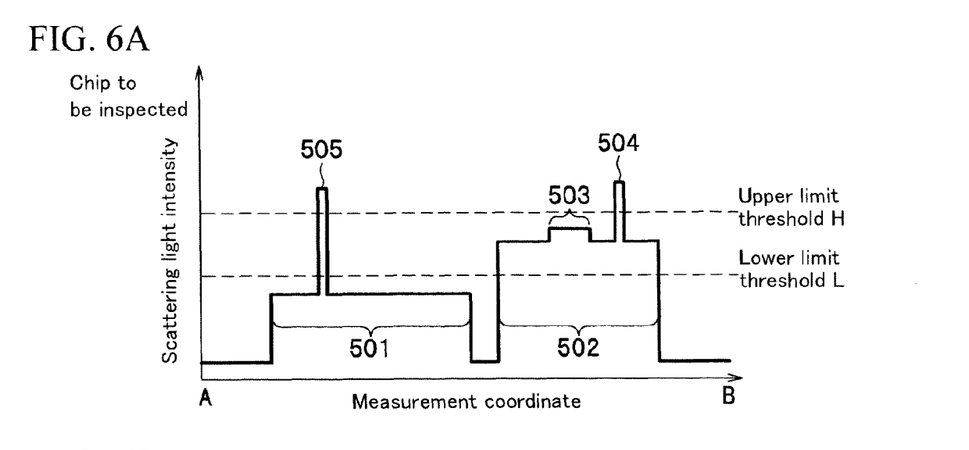
FIG. 6A is a distribution view of scattering light intensity in scanning between A-B of the chip to be inspected shown in FIG. 5A.

In this case, as shown in FIG. 5A, if the spot (measurement coordinate) is scanned in a direction from A to B and the scattering light intensity is measured, the scattering light intensity distribution view can be obtained as shown in FIG. 6A. Scattering light intensity 501 of the memory unit 402 with dense pattern is lower than scattering light intensity 502 of the logic unit 403 with sparse pattern. Therefore, a lower limit threshold L is set to be of amplitude between the scattering light intensity 501 and the scattering light intensity 502; and accordingly, a sparse pattern region like the logic unit 403 can be easily extracted.

In the scattering light intensity 502 of the logic unit 403, the scattering light intensity 503 of the inspection range 406 shows a large value. Therefore, although not shown in the drawing, the lower limit threshold L is set to be of amplitude between the scattering light intensity 502 and the scattering light intensity 503; and accordingly, the inspection range 406 can be easily extracted.

Then, the scattering light intensity is obtained by scanning not only in the direction from A to B, but also scanning the whole one chip of the semiconductor device, for example; and accordingly, the inspection range 406 can be searched mutually exclusive and collectively exhaustive.

In addition, as shown in FIG. 6A, a foreign particle signal 504 caused by a foreign particle and a defect signal 505 caused by a defect are also observed. The scattering light intensities of the foreign particle signal 504 and the defect signal 505 are higher than the scattering light intensity 502 of the logic unit 403 and the scattering light intensity 503 of the inspection range 406. Therefore, the upper limit threshold H is set to be of amplitude between both the scattering light intensities of the foreign particle signal 504 and the defect signal 505 and the scattering light intensity 503 or the scattering light intensity 502; and accordingly, the foreign particle signal 504 and the defect signal 505 can be easily excluded from objects to be extracted.

Figure 6B:
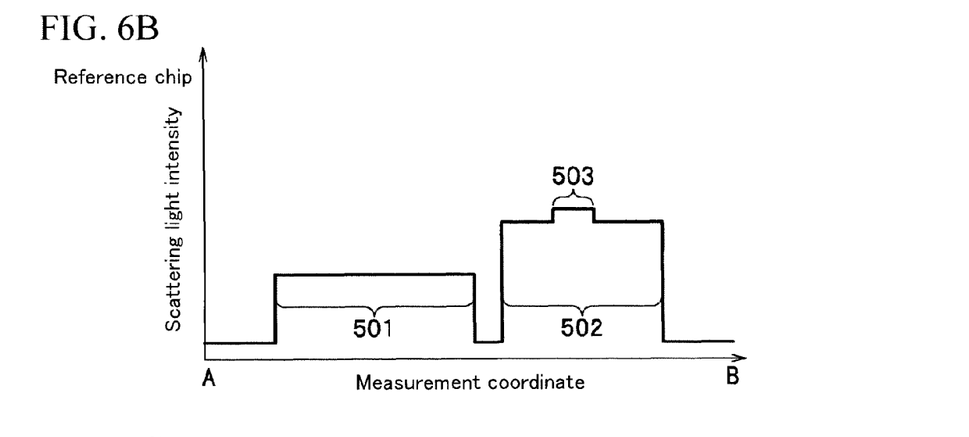
FIG. 6B is a distribution view of scattering light intensity in scanning between A-B of a reference chip shown in FIG. 5A.
Figure 6C:
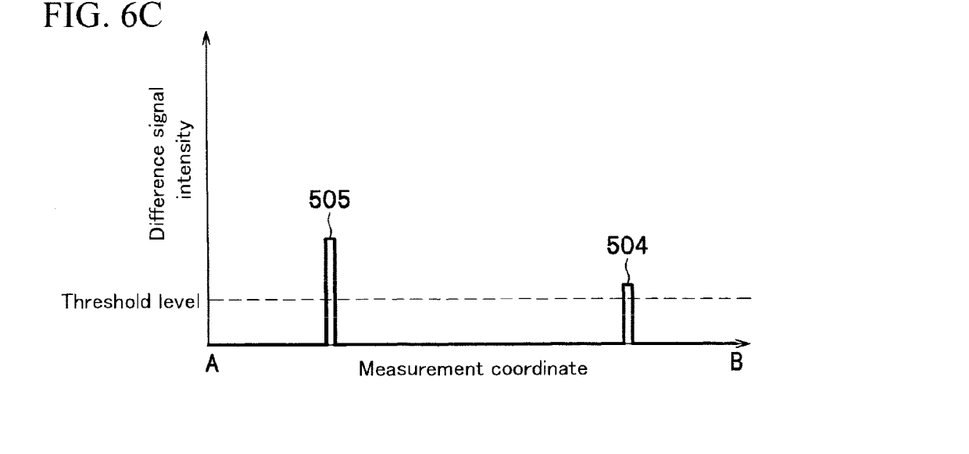
FIG. 6C is a distribution view of difference signal intensity along between A-B shown in FIG. 5A.

By the way, in an ordinary optical wafer surface inspection tool 110, given that scattering light intensity distribution shown in FIG. 6A is a measured result of the chip to be inspected on the wafer 200 (see FIG. 2), scattering light intensity distribution of a reference chip as shown in FIG. 6B is measured in advance of the inspection measurement. A semiconductor chip placed on the same wafer 200 as the chip to be inspected can be used for the reference chip and, more particularly, the semiconductor chip adjacent to the chip to be inspected can be used. In addition, coordinate systems used for measurement coordinates are independent of each other among chips. Then, in order to easily compare the same locations in the chips, coordinate systems which are the same in system are used between a plurality of chips so that their origins are unified to be at the bottom left of the chips. Then, in the ordinary optical wafer surface inspection tool 110, as shown in FIG. 6C, the scattering light intensity of the reference chip is subtracted from the scattering light intensity of the chip to be inspected for each corresponding measurement coordinate, and difference signal intensity is obtained; accordingly, only the scattering light intensities of the foreign particle signal 504 and the defect signal 505 measured in the chip to be inspected can be obtained as the difference signal intensity, and the foreign particle or the defect can be detected. Furthermore, if required, a threshold level is set, and the inspection of the foreign particle or the defect may be performed on the basis of the difference signal intensity larger than the threshold level.

In the before mention, the characteristics of the scattering light intensity of the region where there is no pattern on the semiconductor device (chip) and those of the scattering light intensity of the region where there is a pattern are described. Then afterward, getting back to the flowchart shown in FIG. 3, description will be made about the surface inspection method after its step S2. In the surface inspection method to be described later, the characteristics of the scattering light intensity are skillfully used and the flat inspection ranges are searched.

Figure 7:
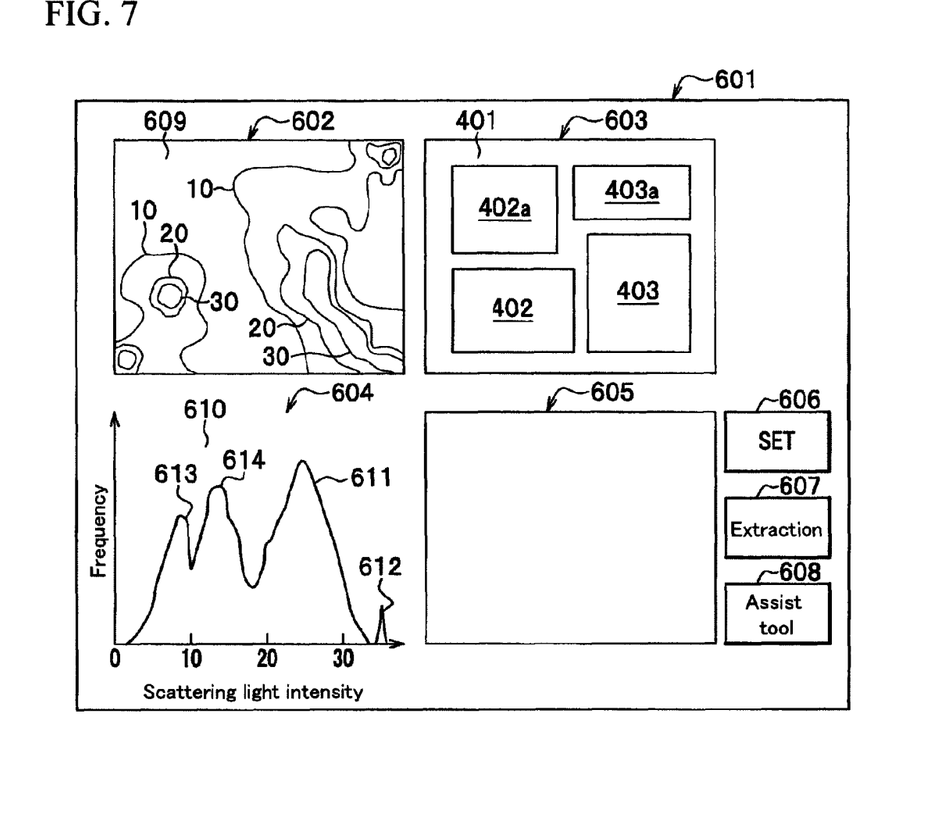
FIG. 7 is a screen display to be displayed on a display unit of the surface inspection tool after measurement of scattering light intensity of a chip to be inspected at step S1 in the surface inspection method according to the embodiment of the present invention.

First, after the measurement of the scattering light intensity at step S1 shown in FIG. 3, at step S2, the tool controller 250 (see FIG. 2) performs screen display of the distribution of the scattering light intensity with respect to the measurement coordinate by a contour chart 609 shown in FIG. 7. FIG. 7 shows a scanned result display screen (GUI) 601 for one chip to be displayed on the information display unit 270 (see FIG. 2). A contour chart display window 602 is provided at the upper left of the scanned result display screen (GUI) 601, and the contour chart 609 is displayed in the contour chart display window 602. Scanning for one chip of the semiconductor chip is performed, and the distribution of scattering light intensity of the scanned result is shown by contours 10, 20, and 30 in the contour chart 609. The scattering light intensities on the contours 10, 20, and 30 become 10, 20, and 30, respectively. A region surrounded by the contour 20 is larger in the scattering light intensity than a region surrounded by the contour 10. A region surrounded by the contour 30 is larger in the scattering light intensity than the region surrounded by the contour 20.

Next, at step S3, the tool controller 250 reads out the whole layout of the chip to be inspected from the design information database 130 (see FIG. 1), and performs screen display in a whole layout display window 603 at the upper right of the scanned result display screen (GUI) 601. The contour chart display window 602 and the whole layout display window 603 are equivalent in window size so that the chips to be objected are displayed in the same size, respectively. In addition, of course, the whole layout may be displayed while being juxtaposed with the contour chart 609, or may be displayed while being superimposed on it.

Next, at step S4, the tool controller 250 performs screen display of a histogram 610 of the scattering light intensity for one chip on the histogram display window 604 at the lower left of the scanned result display screen (GUI) 601. For example, the area of the region surrounded by the contour 10 of the contour chart 609 corresponds to an integration value of frequencies equal to or more than the scattering light intensity of 10 in the histogram 610. Similarly, the area of the region surrounded by the contour 20 corresponds to an integration value of frequencies equal to or more than the scattering light intensity of 20 in the histogram 610; and, the area of the region surrounded by the contour 30 corresponds to an integration value of frequencies equal to or more than the scattering light intensity of 30 in the histogram 610. Furthermore, qualitatively, the logic unit 403 appears as a spectrum 611 with a low pattern density. The memory unit 402 appears as spectra 613 and 614 with a high pattern density. The scattering light intensity of the spectra 613 and 614 being lower than the scattering light intensity of the spectrum 611 is as a result of the characteristics that the higher the pattern density is, the smaller the scattering light intensity becomes, as described in the characteristics of the scattering light intensity. Furthermore, the foreign particle or the defect appears as a foreign particle or defect spectrum 612. The scattering light intensity of the foreign particle or defect spectrum 612 being higher than the scattering light intensity of the spectrum 611 is as described in the characteristics of the scattering light intensity.

Furthermore, although to be described later, an enlarged display window of a partial layout 605 in which a partial layout of a part of the whole layout of the chip to be inspected 401 is enlarged and displayed, a SET button 606 which is making an operator determine the specified inspection range, an extraction button 607 which is for automatically extracting the measurement coordinate having the scattering light intensity between the upper limit threshold H and the lower limit threshold L, and an assist tool button 608 which is for moving to an assist tool are provided at the lower right of the scanned result display screen (GUI) 601.

Figure 8:
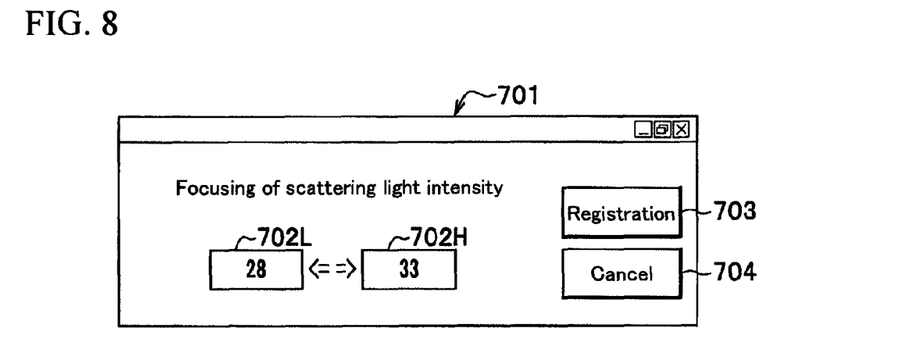
FIG. 8 is a window to be displayed on the display unit of the surface inspection tool at the time of setting support of a lower limit threshold and an upper limit threshold at step S5 in the surface inspection method according to the embodiment of the present invention.

Next, at step S5, the tool controller 250 performs setting support of the lower limit threshold L and the upper limit threshold H. When the extraction button 607 is clicked by the operator, a scattering light intensity focusing window 701 shown in FIG. 8 is appeared. The operator is persuaded to set the lower limit threshold L and the upper limit threshold H by the appearance of the window 701; with reference to the histogram 610 shown in FIG. 7, the operator inputs, for example, 28 in a lower limit threshold setting column 702L as the lower limit threshold L, and inputs, for example, 33 in an upper limit threshold setting column 702H as the upper limit threshold H. Then, when a registration button 703 is clicked by the operator, the lower limit threshold L and the upper limit threshold H are set. In addition, it becomes possible to cancel the inputted lower limit threshold L and the upper limit threshold H by clicking a cancel button 704, and to input again.

Figure 9:
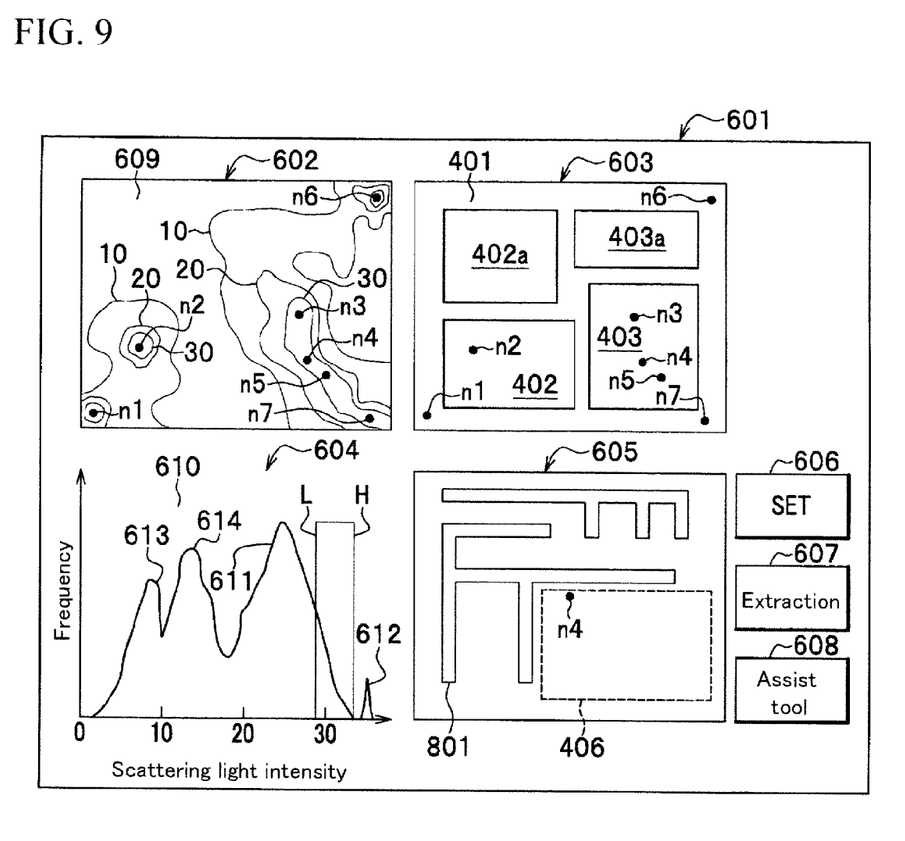
FIG. 9 is a screen display to be displayed on the display unit of the surface inspection tool after extraction of a candidate coordinate at step S6 in the surface inspection method according to the embodiment of the present invention.

Then, the lower limit threshold L and the upper limit threshold H can be image-displayed on a lateral axis (scattering light intensity) in the histogram 610 of the histogram display window 604 shown in FIG. 9.

Next, at step S6, the tool controller 250 extracts measurement coordinates (candidate coordinate) n1 to n7 having the scattering light intensities equal to or more than the lower limit threshold L and equal to or less than the upper limit threshold H.

At step S7, the tool controller 250 displays the extracted candidate coordinates n1 to n7 by dot on both the contour chart 609 and the whole layout of the chip to be inspected 401 as shown in FIG. 9. The candidate coordinates n1 to n7 are displayed while being superimposed on the contour chart 609; and accordingly, the operator can easily confirm that the candidate coordinates n1 to n7 are set at a place where the scattering light intensity is large. Furthermore, the candidate coordinates n1 to n7 are displayed while being superimposed on the whole layout of the chip to be inspected 401; and accordingly, it is possible to understand at a glance where the candidate coordinates n1 to n7 are placed on the whole layout.

At step S8, the inspection range 406 is set in a partial layout 801 including the candidate coordinates n1 to n7 by the tool controller 250. The step S8 may also has screen display of a partial layout at step S9 and setting support of an inspection range at step S10, and may also has a list display at step S11 and determining support of a partial layout at step S12. Furthermore, all in the steps S9 to S12 may be had.

At step S9, the operator clicks one candidate coordinate among a plurality of the candidate coordinates n1 to n7, for example, clicks a dot of the candidate coordinate n4. By this click, the tool controller 250 performs screen display of the partial layout 801 corresponding to the periphery of the candidate coordinate n4 in the enlarged display window of the partial layout 605, and supports inspection range setting for the operator.

At step S10, if the operator wants to set the inspection range 406 in the enlarged display window of the partial layout 605, the operator clicks the SET button 606. By this click, the tool controller 250 sets the inspection range 406 in the enlarged display window of the partial layout 605 as shown in FIG. 9.

Furthermore, it may proceed to step S11 by skipping step S9 and step S10.

Figure 10:
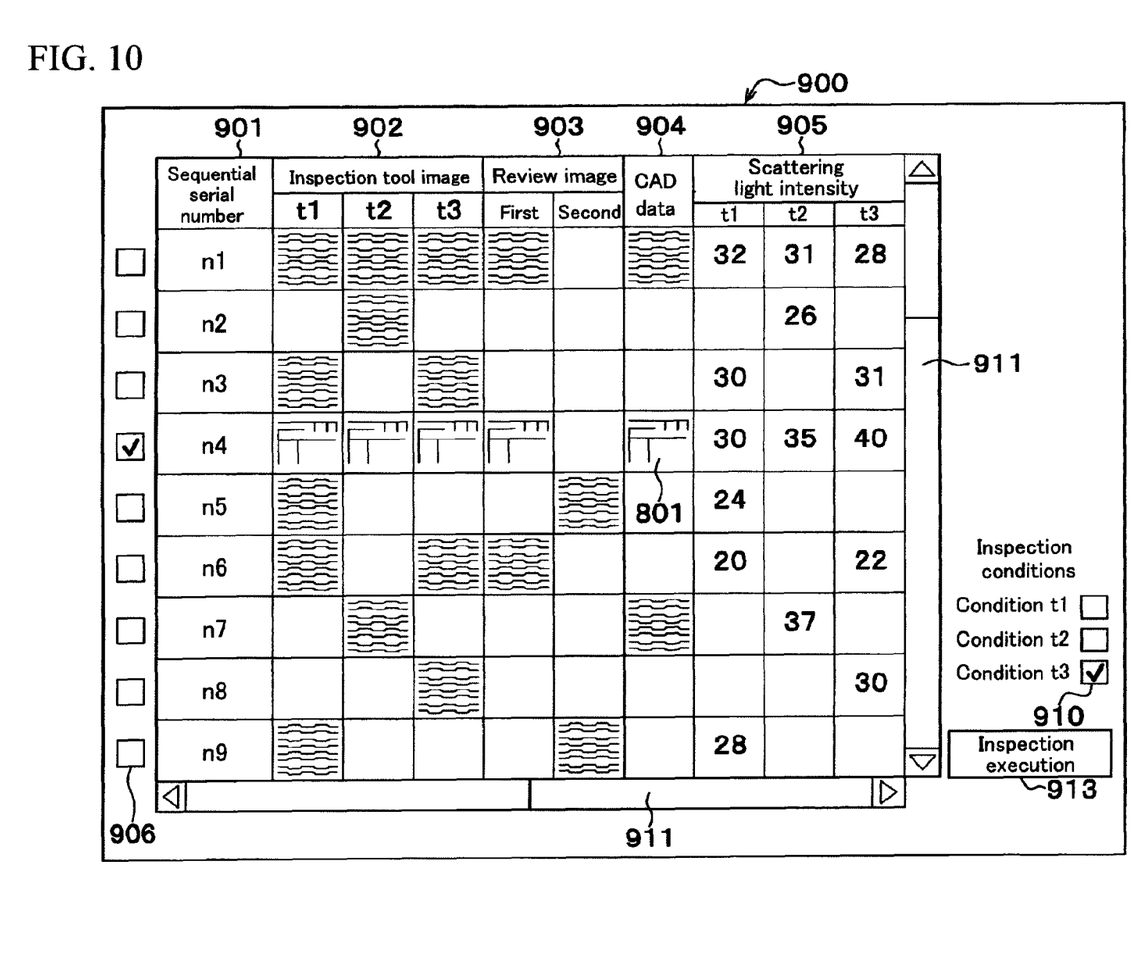
FIG. 10 is a screen display to be displayed on the display unit of the surface inspection tool in displaying a list at step S11 in the surface inspection method according to the embodiment of the present invention.

At step S11, the tool controller 250 performs screen display of an assist tool display screen (GUI) 900 as shown in FIG. 10 on the information display unit 270 by clicking the assist tool button 608 by the operator; and accordingly, the partial layout or the like on the periphery of the candidate coordinates n1 to n9 are list-displayed. Data which is for list-displaying is stored in the list display database 121 shown in FIG. 1; and accordingly, the list display can be easily generated. The assist tool display screen (GUI) 900 includes a sequential serial number display column 901 in which identification numbers of the candidate coordinates n1 to n9 are set; an inspection tool image display column 902 which displays an inspection tool image of the range corresponding to the partial layout on the periphery of the candidate coordinates n1 to n9, which is taken by the optical wafer surface inspection tool 110 (see FIG. 1); a review image display column 903 which displays a review image of the range corresponding to the partial layout, which is taken by the review SEM 150 (see FIG. 1); a partial layout (CAD data) display column 904 which displays a partial layout (CAD data) corresponding to the partial layout 801 shown in FIG. 9; a scattering light intensity display column 905 which displays the scattering light intensities in the candidate coordinates n1 to n9 which have been measured by the optical wafer surface inspection tool 110 (see FIG. 1); and a candidate coordinate selection check column 906 in which the operator selects the candidate coordinates. Furthermore, there is a case where it is measured by the optical wafer surface inspection tool 110 while inspection conditions t1 to t3 being changed, and the inspection tool image and the scattering light intensity may be displayed for each of the inspection conditions t1 to t3.

At step S12, by performing such list display, the operator can easily find the candidate coordinate capable of setting the inspection range 406 (see FIG. 9), for example, n4 in various images (partial layout). The operator clicks the selection check column 906 of the candidate coordinate n4; and accordingly, the tool controller 250 can display a check on the selection check column 906 of the candidate coordinate n4, can support a determination of the partial layout, and can further set the inspection range 406 as shown in FIG. 9.

Furthermore, for example, the operator can easily find the inspection condition t3 with which the scattering light intensity of 40 with the highest sensitivity has been obtained, for example, by watching the scattering light intensities 30, 35, and 40 of the candidate coordinate n4. The operator clicks a selection check column 910 of the inspection condition t3; and accordingly, the tool controller 250 displays a check on the selection check column 910 of the inspection condition t3, and the inspection condition t3 can be set in the inspection conditions. In addition, even when the candidate coordinates n1 to n9 and the inspection conditions t1 to t3 increase, it is possible to handle the list display by a scroll bar 911.

At step S13, the operator clicks an inspection execution button 913 shown in FIG. 10 or the SET button 606 shown in FIG. 9; and accordingly, the tool controller 250 obtains the scattering light intensity within the inspection range 406. Actually, the scattering light intensity only within the inspection range 406 may be measured again, or the scattering light intensity only within the inspection range 406 may be read out from the measured result measured at step S1.

Finally, at step S14, the surface roughness within the inspection range 406 is calculated on the basis of the scattering light intensity within the inspection range 406.

As described above, according to the embodiment, the flat inspection range 406 capable of inspecting the surface roughness, which exists on the wafer with patterns 200 can be easily specified, and the surface roughness in the inspection range 406 can be automatically measured in a nondestructive manner, and with high speed and high accuracy. Then, by use of the measured result of the surface roughness of the wafer 200 measured by the embodiment, semiconductor process fluctuation is monitored; and accordingly, it becomes possible to early detect process abnormality and to improve yield of the semiconductor chip. As described above, the embodiment can be used for semiconductor element inspection and measurement in the manufacturing field of semiconductor chips and semiconductor manufacturing process control.

What is claimed is:

1. A method for acquiring information of roughness of a substrate in which a pattern is formed, the method comprising steps of:
   irradiating the substrate with light;
   detecting light from the substrate to associate the detected light with a coordinate on the substrate;
   processing a result of the detecting step using at least one of a first threshold and a second threshold, wherein the second threshold is less than the first threshold; and
   obtaining position information for acquiring the information of roughness of the substrate using a result of the processing step, wherein:
   the pattern includes a first pattern and a second pattern denser than the first pattern, and
   the second threshold is greater than an intensity of light from the first pattern and is less than an intensity of light from the second pattern.

2. The method according to claim 1, wherein the detecting step further includes corresponding the coordinate on the substrate to design data of the pattern.

3. The method according to claim 1, wherein the first threshold is less than an intensity of light from a defect and is greater than an intensity of light from a surface roughness.

4. An apparatus for acquiring information of roughness of a substrate in which a pattern is formed, the apparatus comprising:
   an optical device which irradiated the substrate with light;
   a detector which detects light from the substrate; and
   a processor,
   wherein the processor is configured to:
      associate a detection result of the detector with a coordinate on the substrate,
      process a result of the association process using at least one of a first threshold and a second threshold, wherein the second threshold is less than the first threshold, and
      obtain position information for acquiring the information of roughness of the substrate from a processing result for the association result, wherein:
   the pattern includes a first pattern and a second pattern denser than the first pattern, and
   the second threshold is greater than an intensity of light from the first pattern and is less than an intensity of light from the second pattern.

5. The apparatus according to claim 4, further comprising:
   a storage which stores design data corresponding to the pattern,
   wherein the processor corresponds the coordinate on the substrate to the design data.

6. The apparatus according to claim 4, the first threshold is less than an intensity of light from a defect and is greater than an intensity of light from a surface roughness.

7. The apparatus according to claim 4, further comprising:
   a display unit,
   wherein the display unit displays the result of the association process as a contour chart window.

8. The apparatus according to claim 5, further comprising:
   a display unit,
   wherein the display unit displays the result of the association process as a contour chart window,
   the display unit further displays the design data as a design data window, and
   the contour chart window and the design window are the same size.

* * * * *